(12) United States Patent
Jaskie et al.

(10) Patent No.: US 11,964,062 B2
(45) Date of Patent: Apr. 23, 2024

(54) ANTIMICROBIAL DEVICE USING ULTRAVIOLET LIGHT

(71) Applicant: LuxHygenix Inc., Scottsdale, AZ (US)

(72) Inventors: James Edward Jaskie, Scottsdale, AZ (US); Michael Ray Johnson, Tempe, AZ (US); Scott Vincent Johnson, Scottsdale, AZ (US); John Jeffrey Martin, Phoenix, AZ (US)

(73) Assignee: LuxHygenix Inc., Scottsdale, AZ (US)

( * ) Notice: Subject to any disclaimer, the term of this patent is extended or adjusted under 35 U.S.C. 154(b) by 0 days.

(21) Appl. No.: 16/991,359

(22) Filed: Aug. 12, 2020

(65) Prior Publication Data

US 2021/0060192 A1 Mar. 4, 2021

Related U.S. Application Data

(60) Provisional application No. 62/895,164, filed on Sep. 3, 2019.

(51) Int. Cl.
*A61L 2/10* (2006.01)
*A61L 2/26* (2006.01)

(52) U.S. Cl.
CPC ............... *A61L 2/10* (2013.01); *A61L 2/26* (2013.01); *A61L 2202/11* (2013.01)

(58) Field of Classification Search
None
See application file for complete search history.

(56) References Cited

U.S. PATENT DOCUMENTS 2,408,809 A * 10/1946 Pierce ............... H01J 25/12
330/45
5,729,094 A * 3/1998 Geis ............... H01J 1/304
313/496

(Continued)

FOREIGN PATENT DOCUMENTS

CN 106935479 A * 7/2017 ............ H01J 63/02
CN 209312705 U * 8/2019

(Continued)

OTHER PUBLICATIONS

Omata et al. ("Ultraviolet electroluminescence from colloidal ZnO quantum dots in an all inorganic multilayer light-emitting device", Appl. Phys. Lett .; Publication [online]. Feb. 6, 2012, [retrieved Oct. 22, 2020 (22.10.2020) (from the IDS of Dec. 29, 2020).*

(Continued)

*Primary Examiner* — Andrew Smyth
(74) *Attorney, Agent, or Firm* — FORTEM IP LLP

(57) ABSTRACT

An antimicrobial device, such as a flashlight, lantern, or lamp, is discussed herein. The antimicrobial device produces light in the ultraviolet (UV) spectrum (i.e., 150-250 nm), including 200-230 nm. The antimicrobial device includes an electron source, an extractor, and a target material. The electron source provides the electrons of sufficient energy to cause a photon to be released, whether by a target or by the electron itself. The extractor extracts the electrons from the electron source. The target material is a component at which the electron is directed. The target material can release a photon having a desired wavelength or within a desired wavelength range or cause the electron to release a photon having a desired wavelength or within a desired wavelength range.

19 Claims, 4 Drawing Sheets

(56) References Cited

U.S. PATENT DOCUMENTS

| | | |
|---|---|---|
| 6,614,039 B2 | 9/2003 | Hollander |
| 7,355,155 B2 | 4/2008 | Wang |
| 7,863,554 B2 | 1/2011 | Watanabe et al. |
| 8,481,985 B2 | 7/2013 | Neister |
| 8,487,285 B2 | 7/2013 | Matsumoto et al. |
| 8,658,086 B2 * | 2/2014 | Bourke, Jr. ............ A23L 3/263 522/42 |
| 8,753,575 B2 | 6/2014 | Neister |
| 8,975,605 B2 | 3/2015 | Neister |
| 9,700,642 B2 | 7/2017 | Neister |
| 10,046,075 B2 | 8/2018 | Nathan et al. |
| 10,220,110 B2 | 3/2019 | Kim et al. |
| 10,987,441 B1 | 4/2021 | Sykes |
| 10,994,153 B2 | 5/2021 | Randers-Pehrson et al. |
| 11,246,951 B2 | 2/2022 | Neister |
| 2002/0113551 A1 * | 8/2002 | Francke ............... H01J 47/02 313/542 |
| 2008/0083887 A1 * | 4/2008 | Komori ............... H05G 2/003 250/504 R |
| 2012/0161609 A1 * | 6/2012 | Ono ..................... H01J 29/20 313/497 |
| 2015/0287587 A1 * | 10/2015 | Honda ................. B05D 5/061 427/157 |
| 2018/0358197 A1 * | 12/2018 | Hu ..................... H01J 35/112 |
| 2019/0198288 A1 * | 6/2019 | Maazouz ............ H01J 37/3056 |
| 2019/0198289 A1 * | 6/2019 | Gledhill ............ G02B 21/0052 |
| 2019/0371569 A1 * | 12/2019 | Bertilson ............ H01J 37/228 |
| 2020/0030469 A1 | 1/2020 | Neister et al. |
| 2020/0171184 A1 | 6/2020 | Tanaka et al. |
| 2021/0060192 A1 | 3/2021 | Jaskie et al. |
| 2021/0339045 A1 | 11/2021 | Randers-Pehrson et al. |
| 2021/0346544 A1 | 11/2021 | Anton |
| 2021/0346561 A1 | 11/2021 | Callahan et al. |
| 2021/0369894 A1 | 12/2021 | Lee et al. |
| 2021/0379215 A1 | 12/2021 | Kelleher et al. |
| 2021/0402019 A1 | 12/2021 | Rosenbaum |
| 2022/0001069 A1 | 1/2022 | Allen et al. |
| 2022/0062478 A1 | 3/2022 | Eltorai et al. |
| 2022/0072186 A1 | 3/2022 | Maa et al. |
| 2022/0096678 A1 | 3/2022 | Kea et al. |
| 2022/0125963 A1 | 4/2022 | Choi et al. |
| 2022/0133920 A1 | 5/2022 | Neister |
| 2022/0143232 A1 | 5/2022 | Neister |
| 2022/0143239 A1 | 5/2022 | Gunawan et al. |
| 2022/0152233 A1 | 5/2022 | Wunderer et al. |

FOREIGN PATENT DOCUMENTS

| | | | |
|---|---|---|---|
| EP | 1666074 B1 | | 5/2008 |
| EP | 1686202 B1 | | 3/2011 |
| EP | 3581624 B1 | | 8/2021 |
| EP | 3960206 A2 | | 3/2022 |
| EP | 3988125 A1 | | 4/2022 |
| EP | 4000644 A1 | | 5/2022 |
| JP | 2006-127924 | | 5/2006 |
| JP | 2006127924 A | * | 5/2006 |
| KR | 101327308 B1 | * | 11/2013 |
| WO | 2005031881 A3 | | 5/2005 |
| WO | 2018110725 A1 | | 6/2018 |
| WO | 2021230836 A1 | | 11/2021 |
| WO | 2022043168 A1 | | 3/2022 |
| WO | 2022046217 A1 | | 3/2022 |

OTHER PUBLICATIONS

Lugolole et al., ("The Effect of Thickness of Aluminium Films on Optical Reflectance" Journal of Ceramics; Publication [online], Feb. 9, 2015 (Sep. 2, 2015) [retrieved Oct. 22, 2020 (Oct. 22, 2020)).*

Omata et al. ("Ultraviolet electroluminescence from colloidal ZnO quantum dots in an all inorganic multilayer light-emitting device", Appl. Phys. Lett.; Publication [online]. Feb. 6, 2012, [retrieved Oct. 22, 2020 (Oct. 22, 2020).*

Omata, T. et al., "Ultraviolet electroluminescence from colloidal ZnO quantum dots in an all inorganic multilayer light-emitting device", Appl. Phys. Lett.; Publication [online]. Feb. 6, 2012, [retrieved Oct. 22, 2020 (Oct. 22, 2020)]. Retrieved from the internet: <URL:https://aip.scitation.org/doi/10.1063/1.3682307>; DOI: 10.1063/1.3682307.

Lugolole, R. et al., "The Effect of Thickness of Aluminium Films on Optical Refectance" Journal of Ceramics; Publication [online], Feb. 9, 2015 (Feb. 9, 2015) [retrieved Oct. 22, 2020 (Oct. 22, 2020)]. Retrived from the Internet: <URL:https://www.hindawi.com/journals/jceram/2015/213635/>; DOI: 10.1155/2015/213635.

International Search Report and Written Opinion dated Dec. 14, 2020, International Application No. PCT/US20/48988, International filing date Sep. 2, 2020.

* cited by examiner

ANTIMICROBIAL DEVICE USING ULTRAVIOLET LIGHT

CROSS-REFERENCE TO RELATED APPLICATIONS

This application claims the benefit of U.S. Provisional Patent Application Ser. No. 62/895,164, filed Sep. 3, 2019, the contents of which are herein incorporated by reference in their entirety.

BACKGROUND

Current antimicrobial devices use mercury, an excited dimer (i.e., an excimer), or an excited complex (i.e., an exciplex, such as KrBr*, ArF*, or KrF*) formation to create ultraviolet light. During this process, an electron transitions from an excited excimer or exciplex state to a weakly bound ground state, thereby causing the release of energy in the form of a photon. The amount of energy of the photon is directly proportional to the photon's electromagnetic frequency, which is inversely proportional to the wavelength.

The device may produce light having a wavelength that is harmful to human cells or components thereof, including deoxyribonucleic acid (DNA), ribonucleic acid (RNA), or both. The device may produce light having an intensity lower than what is required for sterilization, disinfecting, or antimicrobial purposes. Therefore, the limitations of the antimicrobial device may result in limited efficacy, whether due to a harmful wavelength, reduced intensity, or the like.

What is needed is a more efficient antimicrobial device.

DETAILED DESCRIPTION

An antimicrobial device, such as a flashlight, lantern, or lamp, is discussed herein. The antimicrobial device produces ultraviolet (UV) light having a wavelength within a desired wavelength range 150-250 nanometer (nm), including 200-230 nm. The antimicrobial device includes an electron source, an extractor, and a target material. The electron source provides free electrons. The free electrons can be used to cause the release of a photon having a wavelength within the desired wavelength range, whether by a target material or by the electron itself. The extractor extracts the electrons from the electron source. The target material is a component at which the free electrons are directed. The target material can release a photon having a wavelength within the desired wavelength range or cause the electron to release a photon having a wavelength within the desired wavelength range. In one example, the target material releases a photon when struck by or stimulated by a free electron provided by the electron source. In another example, the target material can decelerate the free electron, thereby causing the electron to emit a photon. With each deceleration event, the electron loses energy but continues to be able to produce these photons until a minimum electron energy is reached.

The antimicrobial device can control the energy of the free electrons provided by the electron source or select materials to emit photons having a given wavelength or wavelength range. This control allows the antimicrobial device to produce UV light having a specific wavelength. The UV light is not harmful to human cells (including the DNA, RNA, or both), has an intensity high enough to properly disinfect (or sterilize, where appropriate) a surface, a liquid, air, gas, the like, or combinations or multiples thereof.

By adjusting the temperature of the thermionic emitter, the accelerating voltages on the freed free electrons, the number and density of the quantum dots and the quantum dot material and size, any desired level of far ultra-violet light intensity can be reached. This creates a light source, or lamp, which can produce a range from a very dim to a very bright light intensity, for any selected wavelength in the desired range or even a distribution of wavelengths as desired for disinfection purposes.

Figure 1A:
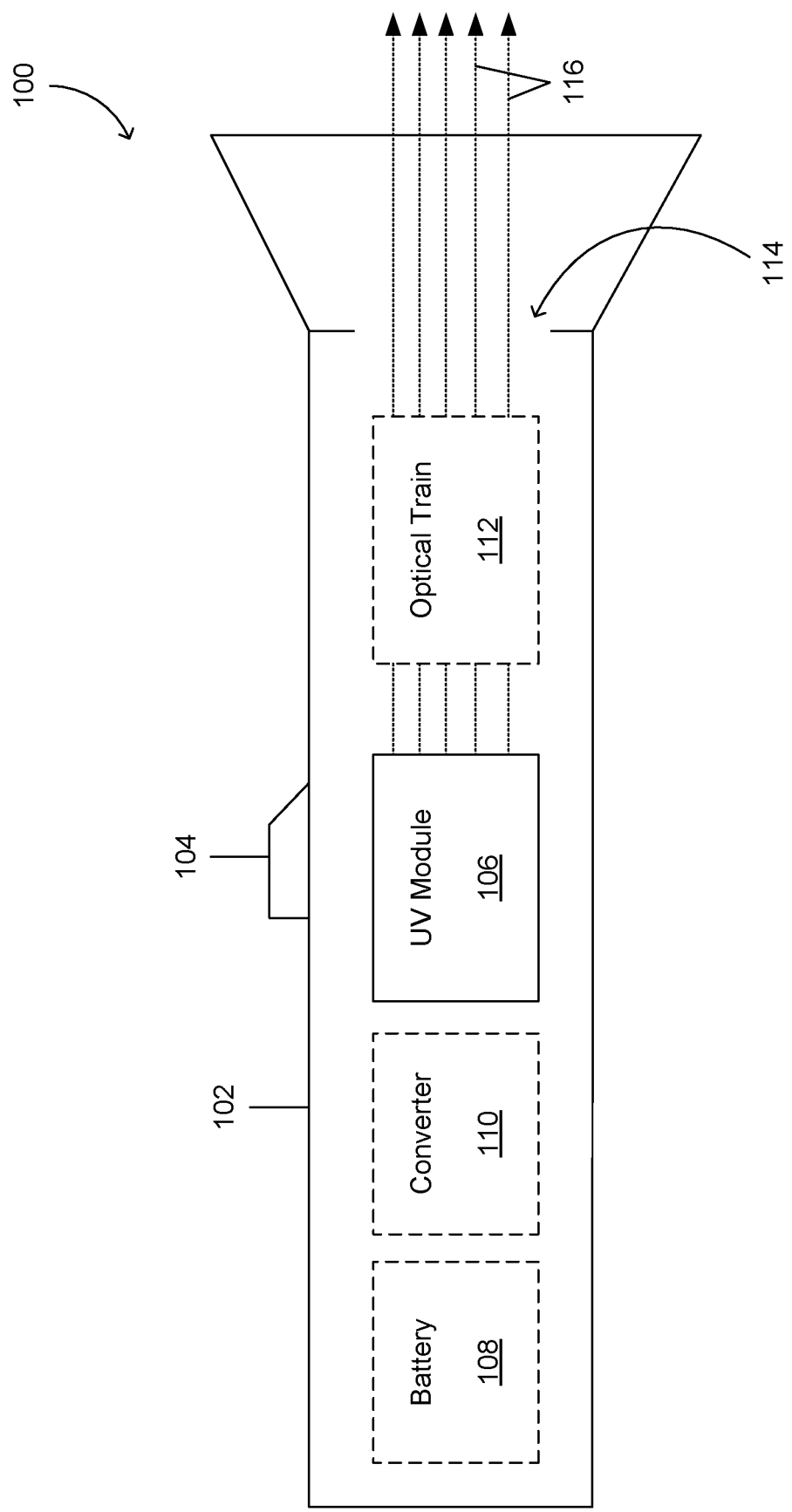
FIG. 1A illustrates an example antimicrobial device.
Figure 1B:
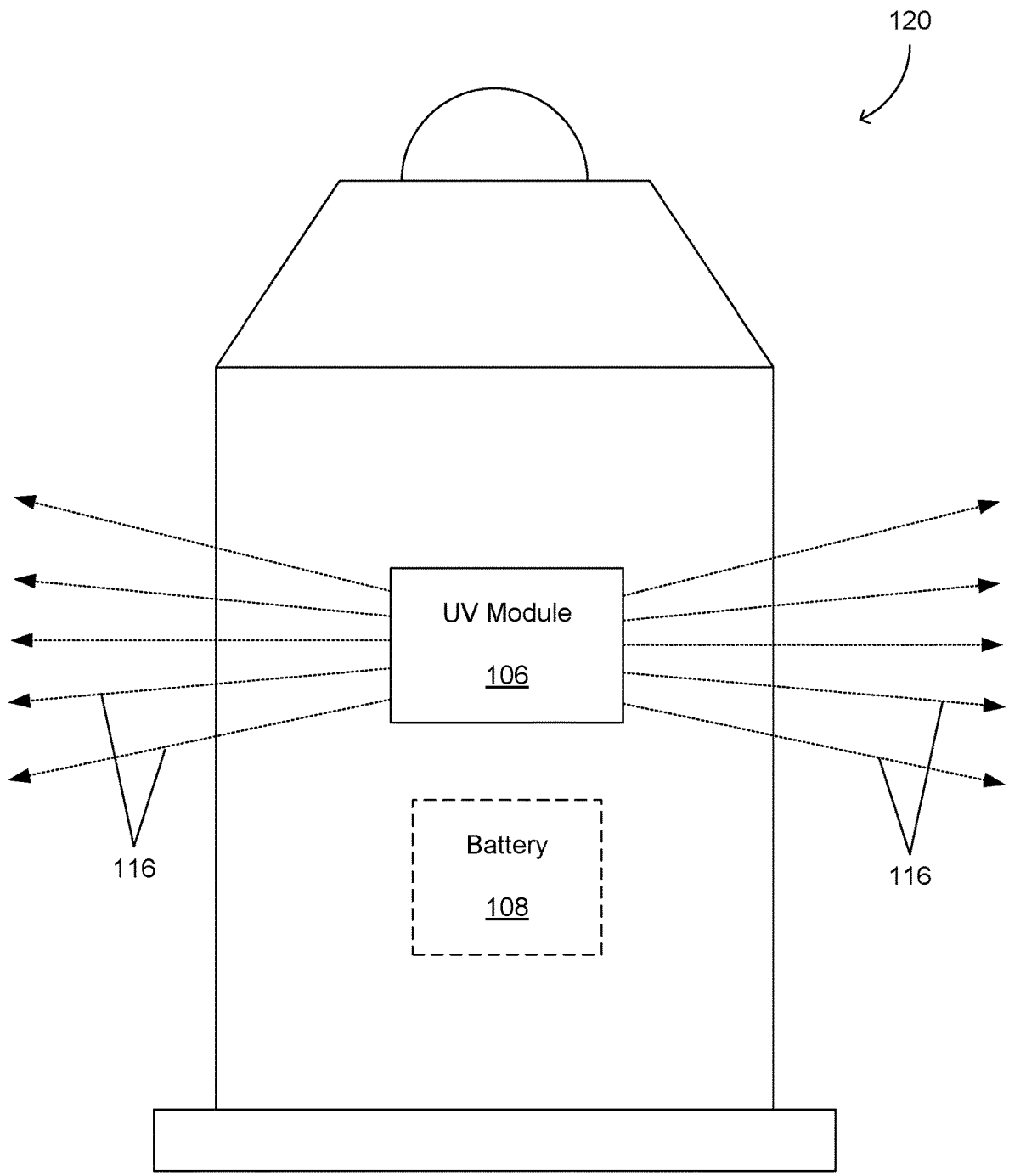
FIG. 1B illustrates an example antimicrobial device.

FIG. 1A shows an antimicrobial device 100, such as a flashlight. FIG. 1B shows another antimicrobial device 120, such as a lantern. The antimicrobial device 100 includes a UV module 106 and a main body 102 having a power switch 104. The antimicrobial device 100 can also include a battery 108, a converter 110, or both. The power switch 104 controls the flow of electricity from a power source, whether the battery 110 or an external power supply via the converter 110, to the UV module 106. In one example, the battery 108 is an internal power source. The battery 108 can be rechargeable or not rechargeable. The battery 108 can also be removable or fixed internally. In another example, the converter 110 can be connected to an external power source, such as an electrical outlet. The converter 110 can include a rectifier to convert AC power to DC power. In yet another example, the antimicrobial device 100 can include both the battery 108 and the converter 110, such that the antimicrobial device 100 includes both an internal power source and can be connected to an external power source. The antimicrobial device 100 can therefore be portable, rechargeable, the like, or combinations thereof.

Figure 2:
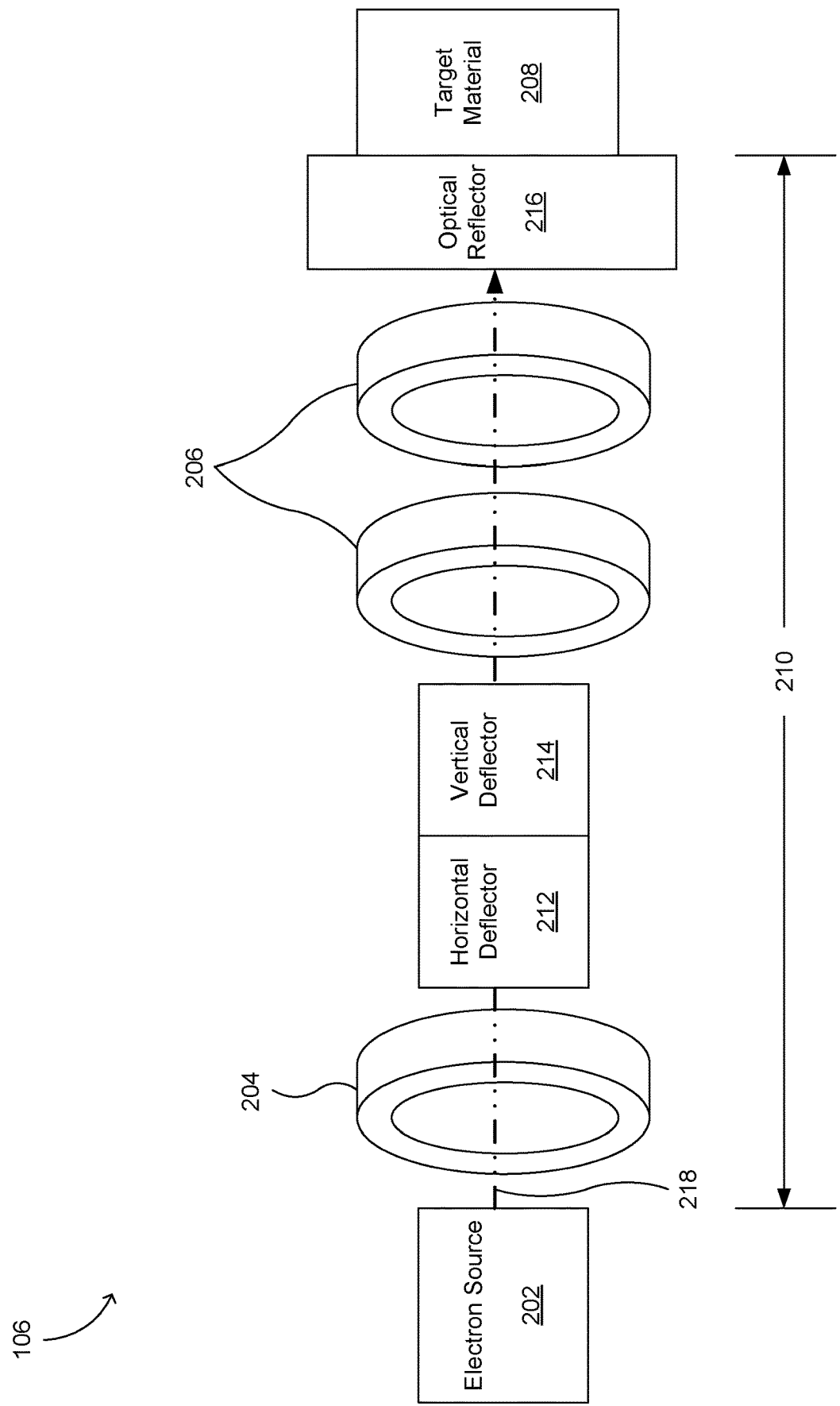
FIG. 2 illustrates an example UV module.

The UV module 106 generates the UV light for disinfection. FIG. 2 shows the UV module 106. The UV module 106 includes an electron source 202, an extractor 204, and a target material 208. The electron source 202 provides free electrons. Free electrons are electrons that are not attached to an ion, atom, or molecule and are free to move under the influence of an applied electric or magnetic field. The free electrons can be used to cause the release of a photon having a wavelength within the desired wavelength range (i.e., 150-250 nm, including 200-230 nm), whether by a target or by the free electron itself. Free electrons can be generated by heating the electron source 202 (such as by a heating element), by applying an electromagnetic field to the electron source 202 (e.g., increasing positive charge on an anode in the presence of a carbon nanotube, or a magnetic field generator), by chemical stimulation (such as by a chemical stimulant), the like, or combinations or multiples thereof. The electron source 202 can include a cathode (e.g., hot cathode, a thermionic cathode, or the like), a filament (e.g., a hot filament), a nanotube, a photoelectrical emitter, the like, or combinations or multiples thereof. The electron source 202 can be composed of tungsten, lanthanum hexaboride, carbon, the like, or combinations or multiples thereof.

The extractor 204, such as a gate, extracts the free electrons from the electron source 202. To extract the free electrons, the extractor 204 can generate a magnetic field, be positively charged, or have a greater electrical potential than the electron source 202. The extractor 204 can be a sleeve, a tube, donut-shaped, or the like to permit the extracted free electrons to pass through the extractor 204 and towards the target material 208.

When the free electrons stimulate the target material 208, the target material 208 releases a photon having a wavelength within a desired wavelength range (e.g., 150-250 nm, including 200-230 nm). The wavelength of the photon can be based on the type of target material 208, the energy with which the free electron strikes or stimulates the target material 208, the energy lost when the free electron decelerates, the like, or combinations or multiples thereof. The target material 208, such as a solid state material, phosphoresces when stimulated, such as by a free electron or light source. The target material 208 can be calcium fluoride, crystalline (e.g., boron nitride, aluminum nitride, or the like), a quantum dot, a phosphor, a scintillator (e.g., a bulk photonic material, including boron nitride, barium fluoride, or the like), plasma, a wide band gap energy material (e.g., aluminum nitride, boron nitride, diamond, or the like), the like, or combinations or multiples thereof.

In one example, the target material 208 releases photons having a wavelength within the desired range. When the free electron has an energy of 8.226 electronvolts (eV) or greater, a photon released from the target material 208 has a wavelength of 150 nm. When the free electron has an energy of 4.959 eV or greater, a photon released from a target material 208 has a wavelength of 250 nm. When the free electron has an energy of 6.199 eV or greater, a photon released from a target material 208 has a wavelength of 200 nm. When the free electron has an energy of 5.391 eV or greater, a photon released from the target material 208 has a wavelength of 230 nm. Therefore, the energy of the free electron, upon striking or stimulating the target material 208, can be at least 4.95 eV, including 5.3 eV to 12.5 eV. The target material 208 converts the energy of the free electron to an appropriate number of photons carrying the energy away from the target material 208. Alternatively, the free electron energy (FEE) can be greater than or equal to the energy required to cause a photon to be emitted having a wavelength (A) within the desired wavelength range times the number of photons emitted at the desired wavelength. In other words, FEE=(Energy of Photon with Wavelength A)×(Number of Photons)

In another example, the target material 208 can be composed of one or more materials which, whether alone or together, release a photon having a wavelength within the desired wavelength range. The wavelength of the photon is based on the one or more properties of the target material 208, including size, type of material, the like, or combinations or multiples thereof. For example, the target material 208 can be quantum dots. Quantum dots are nanometer-sized semiconductor particles (e.g., 1-10 nm). The quantum dots can be unary (e.g., composed of a material from a single periodic group), binary (e.g., composed of two materials, each material from a different periodic group), ternary (e.g., composed of three materials, each material from a different periodic group), quaternary (e.g., composed of four materials, each material from a different periodic group), or the like. For example, the quantum dots can be composed of a material from periodic group IV (e.g., Si, Ge, C, or the like). As another example, the quantum dots can be made from periodic groups II-VI, III-V, IV-VI, or the like, including, without limitation, cadmium selenide, cadmium sulfide, cadmium telluride, zinc sulfide, zinc telluride, indium arsenide, gallium nitride, boron nitride, aluminum nitride, and indium phosphide.

Differences in properties of quantum dots, such as size, materials, or both, can shift the wavelengths of the photons, thereby permitting quantum dots to be manufactured or selected to release photons having specific wavelengths within the desired wavelength range (e.g., 150-250 nm, including 200-230 nm).

In yet another example, the target material 208 can have defects or impurities that produce photons having a wavelength within the desired wavelength range or electrons and electron holes (i.e., absent electrons) that recombine to produce photonic radiation having a wavelength within the desired wavelength range.

In still another example, the target material 208 can be selected to decelerate the free electrons. The deceleration (i.e., decrease in kinetic energy) creates a photon having a wavelength within the desired wavelength range, such as by creating bremsstrahlung radiation. With each deceleration event, the electron loses energy but continues to be able to produce these photons until a minimum electron energy is reached. For example, the target material 208 can be plasma having a charge to decelerate the free electrons. The plasma can have some or all of the atoms excited to higher energy level by the free electrons, which then releases the energy in the desired wavelength range. The plasma can be non-Maxwellian. Alternatively, the target material 208 can have an atomic mass to decelerate the free electrons (i.e., free electron scattering). Alternatively, the target material 208 can be a decelerating electrode, which generates a magnetic or electric field that causes the free electron to decelerate.

The UV module 106 can also include a space 210 between the electron source 202 and the target material 208. The space can be greater than or equal to 0.1 nm, including up to 10 cm. The space 210 can include a vacuum, a dielectric (e.g., a solid dielectric), path electrodes 206, the like, or combinations or multiples thereof.

The path electrodes 206 assist the free electron in moving along a transmission path 218 across the space 210, such as from the electron source 202 towards the target material 208. The path electrodes 206 can increase, decrease, or maintain the energy of the free electron as the free electron travels across the space 210. For example, an initial energy of a free electron can create a photon having an undesired wavelength. However, the energy of the free electron can be changed, whether increased or decreased, to a second energy to create a photon having a wavelength within the desired wavelength range, such as when stimulating the target material or creating bremsstrahlung radiation.

The UV module 106 can also include an optical reflector 216. The optical reflector 216 reflects the photons released from the target material 208 outwardly from the antimicrobial device 100. The photons can be reflected towards a window, an opening, an aperture, or the like of the antimicrobial device 100. The optical reflector 216 can be flat, spherical, or parabolic. The optical reflector 216 can be composed of aluminum or any other appropriate material. In one example, as shown in FIG. 2, the optical reflector 216 is in the transmission path 218 of the free electron and permits the free electrons to pass through to the target material 208.

Figure 3:
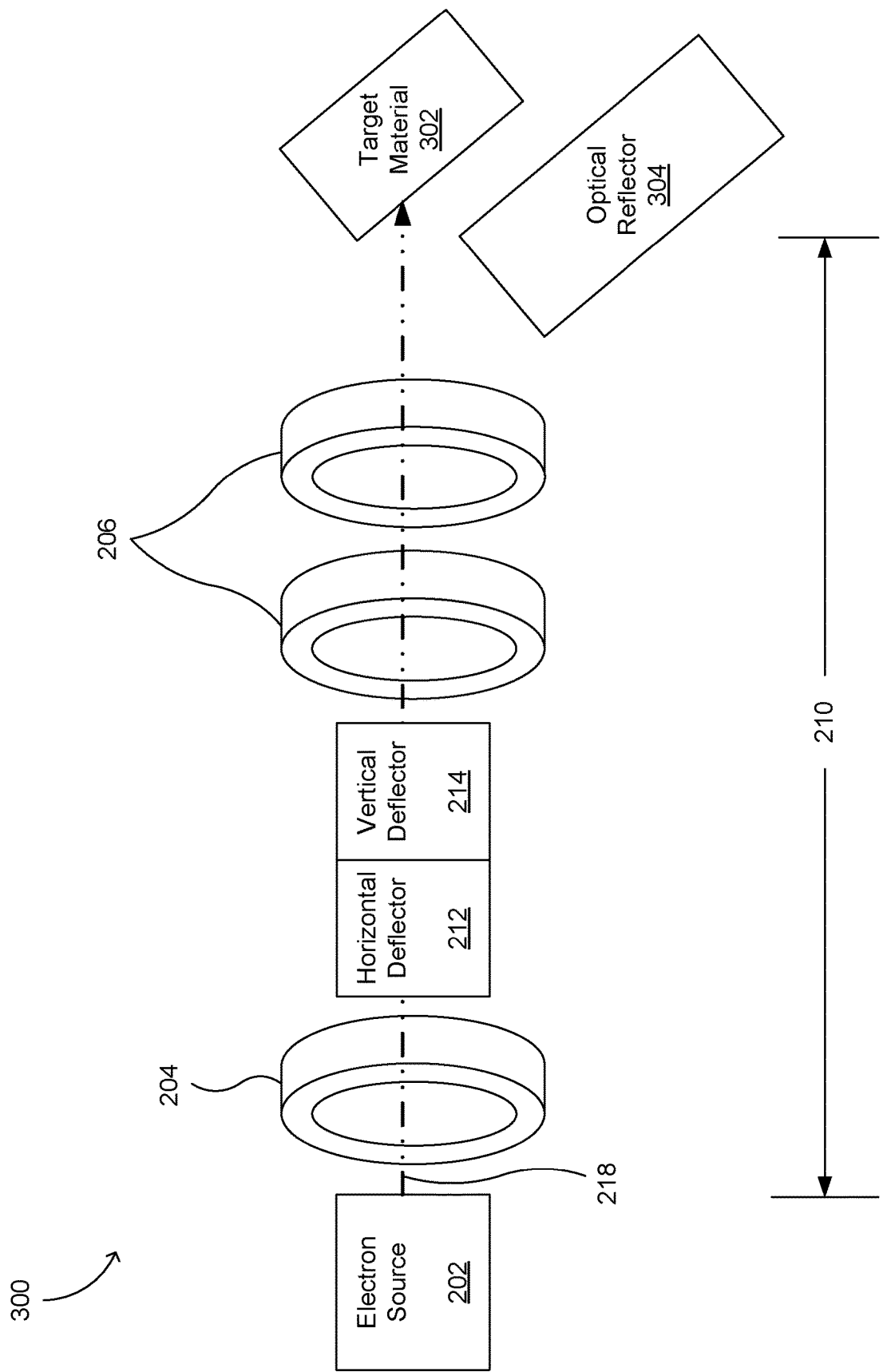
FIG. 3 illustrates an example UV module.

In another example, FIG. 3 shows a UV module 300. The UV module 300 is similar to the UV module 106, except that the UV module 300 includes an optical reflector 304 that is offset from the transmission path 218 of the free electron, such as when a target material 302 is at an angle not perpendicular to the transmission path 218 of the free electron (e.g., 1-89°, including 10°, 20°, 30°, 33°, 45°, or the like).

Returning to FIG. 2, the UV module 106 can also include a horizontal deflector 212, a vertical deflector 214, or both (e.g., deflector yoke). The horizontal deflector 212 can direct or deflect the free electrons left and right as the free electrons travel from the electron source 202 toward the target material 208. The vertical deflector 214 can direct the free electrons up and down as the free electrons travel from the electron source 202 toward the target material 208.

Though the horizontal and vertical deflectors 212, 214 are shown as being in line with the other components of the UV module 106, the horizontal and vertical. deflectors 212, 214 can be outside of the other components (e.g., each deflector has two plates, such that one plate of the horizontal deflector 212 is to the left and one plate is to right of the space 210 or the path electrodes 206, and such that one plate of the vertical deflector 214 is to the top and one plate is to bottom of the space 210 or the path electrodes 206).

Though the horizontal and vertical deflectors 212, 214 are shown as being positioned between the extractor 204 and the path electrodes 206, the horizontal and vertical deflectors 212, 214 can be positioned in front of, between, or after any other components of the UV module 106. The horizontal and vertical deflectors 212, 214 can also be positioned at different locations.

Returning to FIG. 1A, the antimicrobial device 100 can include an optical train 112. The optical train 112 can include lenses, mirrors, filters, the like, or combinations or multiples thereof to direct photons 116 to an aperture 114 of the antimicrobial device 100. The aperture 114 is an opening through which the photons or light is emitted from the antimicrobial device 100 to the surrounding environment.

Embodiments of the invention can include a non-transitory computer readable medium, which can store instructions for performing the above-described methods and any steps thereof, including any combinations of the same. For example, the non-transitory computer readable medium can store instructions for execution by one or more processors or similar devices.

Further embodiments of the present invention can also include the one or more user components which read out and execute computer executable instructions, such as a non-transitory computer-readable medium, recorded or stored on a storage medium (which may be the same as or different than the storage medium for storing images or files, as discussed above), to perform the functions of any embodiment or example. The component may include one or more of a central processing unit (CPU), micro processing unit (MPU), or other circuitry, such as a processor, and may include a network of separate user equipment or servers or separate computer processors. The computer executable instructions may be provided to the component, for example, from the storage medium.

Though certain elements, aspects, components or the like are described in relation to one embodiment or example of an antimicrobial device, those elements, aspects, components or the like can be including with any other antimicrobial device, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments or examples are presented by way of examples for purposes of illustration and description. They are not intended to be exhaustive of or to limit this disclosure to the precise forms described. Many modifications and variations are possible in view of the above teachings. The embodiments or examples are shown and described in order to best explain the principles of this disclosure and practical applications, to thereby enable others skilled in the art to best utilize this disclosure and various embodiments or examples with various modifications as are suited to the particular use contemplated. It is intended that the scope of this disclosure be defined by the following claims and their equivalents.

What is claimed is:

1. An antimicrobial device, comprising: an ultraviolet (UV) module, comprising:
    an electron source to provide a free electron;
    an extractor to extract the free electron from the electron source and direct the free electron in a first direction towards a target material with a first amount of energy;
    one or more path electrodes disposed between the extractor and the target material, the one or more path electrodes configured to increase the energy of the free electron from the first amount of energy to a second amount that is at least 5.3 electron volts (eV);
    the target material comprising a quantum confined material or quantum dot configured to receive the free electron and, in response, produce a photon having a wavelength within a wavelength range of 200-230 nanometers (nm);
    an exit window disposed on the target material, the exit window configured to permit photons produced by the target material to pass therethrough; and
    a parabolic optical reflector disposed entirely between the extractor and the target material, the parabolic optical reflector configured to permit free electrons to pass along a transmission path to the target material and to reflect photons produced by the target material outwardly through the exit window.

2. The antimicrobial device of claim 1, wherein the target material includes a defect or impurity that, when stimulated or struck by the free electron, produces the photon.

3. The antimicrobial device of claim 1, wherein the target material includes an electron-electron hole pair that, when struck or stimulated by the free electron, recombines to produce the photon.

4. The antimicrobial device of claim 1, wherein the target material is a wide band gap energy material that produces the photon when stimulated by the free electron.

5. The antimicrobial device of claim 1, wherein the target material causes the free electron to decelerate and to emit the photon.

6. The antimicrobial device of claim 1, wherein the electron source is a carbon nanotube.

7. The antimicrobial device of claim 1, wherein the UV module further comprises a space between the electron source and the target material.

8. The antimicrobial device of claim 7, wherein the space includes a vacuum, a dielectric, or both.

9. The antimicrobial device of claim 7, wherein the space includes a path electrode including an electric or magnetic field to assist the free electron in moving across the space.

10. The antimicrobial device of claim 1, wherein the UV module further comprises a heating element, a chemical stimulant, or a magnetic field generator to cause the electron source to produce the free electron.

11. The antimicrobial device of claim 1, wherein the target material comprises a boron nitride quantum dot or quantum confined material.

12. A device, comprising:
an electron source configured to provide a free electron;
an extractor configured to direct the free electron from the electron source along a transmission path towards a target material that is spaced apart from the electron source;
the target material comprising one or more boron nitride quantum dots or quantum confined material configured to receive the free electron and, in response, produce one or more photons having a wavelength within a wavelength range of 200-230 nanometers (nm); and
a parabolic optical reflector disposed entirely between the extractor and the target material, the parabolic optical reflector configured to reflect photons produced by the target material outwardly from the device; and
wherein the axis of symmetry of the parabolic optical reflector is parallel to a transmission path from the extractor to the target material.

13. The device of claim 12, wherein the parabolic optical reflector permits the free electron to pass therethrough before reaching the target material.

14. The antimicrobial device of claim 1, wherein the parabolic optical reflector permits the free electron to pass therethrough before reaching the target material.

15. The antimicrobial device of claim 1, wherein the parabolic optical reflector is positioned such that the free electrons does not pass through the parabolic optical reflector while passing along the transmission path to the target material.

16. The antimicrobial device of claim 1, wherein the extractor has a tubular shape.

17. The antimicrobial device of claim 1, wherein the extractor is configured to generate a magnetic field.

18. The antimicrobial device of claim 1, wherein the parabolic optical reflector is coaxial with both the extractor and the target material.

19. The antimicrobial device of claim 1, wherein the axis of symmetry of the parabolic optical reflector is parallel to a transmission path from the extractor to the target material.

* * * * *